(12) United States Patent
Patterson

(10) Patent No.: US 7,115,561 B2
(45) Date of Patent: Oct. 3, 2006

(54) MEDICAMENT COMPOSITION AND METHOD OF ADMINISTRATION

(76) Inventor: James A. Patterson, 2612 Tanglewood Dr., Sarasota, FL (US) 34239

( * ) Notice: Subject to any disclaimer, the term of this patent is extended or adjusted under 35 U.S.C. 154(b) by 0 days.

(21) Appl. No.: 10/947,484

(22) Filed: Sep. 22, 2004

(65) Prior Publication Data

US 2006/0063698 A1    Mar. 23, 2006

(51) Int. Cl.
  *A61K 38/00*  (2006.01)
  *A61K 38/20*  (2006.01)
  *A61K 9/14*   (2006.01)
  *A01N 37/18*  (2006.01)

(52) U.S. Cl. .................. 514/2; 424/434; 424/489; 514/3; 514/951

(58) Field of Classification Search .............. 514/2, 514/3, 951; 424/434, 489
See application file for complete search history.

(56) References Cited

U.S. PATENT DOCUMENTS

| | | |
|---|---|---|
| 4,153,689 A | 5/1979 | Hirai et al. |
| 4,613,500 A | 9/1986 | Suzuki et al. |
| 5,179,079 A | 1/1993 | Hansen et al. |
| 5,204,108 A | 4/1993 | Illum |
| 5,578,567 A | 11/1996 | Cardinaux et al. |
| 5,603,943 A | 2/1997 | Yanagawa |
| 5,629,011 A | 5/1997 | Illum |
| 5,648,095 A | 7/1997 | Illum |
| 5,661,130 A | 8/1997 | Meezan et al. |
| 5,690,954 A | 11/1997 | Illum |
| 5,707,644 A | 1/1998 | Illum |
| 5,725,852 A | 3/1998 | Igari et al. |
| 5,744,166 A | 4/1998 | Illum |
| 5,804,212 A | 9/1998 | Illum |
| 5,908,824 A | 6/1999 | Yanagawa |
| 5,942,242 A * | 8/1999 | Mizushima et al. ........ 424/434 |
| 5,948,749 A | 9/1999 | Igarashi et al. |
| 5,997,848 A | 12/1999 | Patton et al. |
| 6,197,328 B1 | 3/2001 | Yanagawa |
| 6,264,975 B1 * | 7/2001 | Boucher, Jr. ............. 424/434 |
| 6,375,985 B1 | 4/2002 | Bomberger et al. |
| 6,416,742 B1 | 7/2002 | Stefely et al. |
| 6,428,780 B1 | 8/2002 | Leone-Bay et al. |
| 6,428,805 B1 | 8/2002 | Dohi et al. |
| 6,506,730 B1 | 1/2003 | Lee et al. |
| 6,521,597 B1 | 2/2003 | Vickery et al. |
| 6,589,559 B1 | 7/2003 | Yanagawa |
| 6,699,467 B1 | 3/2004 | Leone-Bay et al. |
| 2002/0012688 A1 | 1/2002 | Dohi et al. |
| 2004/0063615 A1 | 4/2004 | Oki et al. |

FOREIGN PATENT DOCUMENTS

CA    2378001 A1    11/2001

OTHER PUBLICATIONS

Takenaga et al. Microparticle resins as a potential nasal drug delivery system for insulin Journal of Controlled Release 1998, 52, 81-87.*
Dow Chemical Company Ion Exchange Media DOWEX.*

* cited by examiner

*Primary Examiner*—Johann Richter
*Assistant Examiner*—Ernst Arnold
(74) *Attorney, Agent, or Firm*—Charles J. Prescott

(57) ABSTRACT

A medicament powder, system and method for nasal administration of a pharmacologically active peptide across the nasal mucous membrane. A free-flowing powder having a low moisture content includes a cross-linked cation exchange resin in anionic form and a pharmacologically active peptide in cationic form ionically bound together. The particles of the powder function as carriers of the peptide during nasal administration. The cation exchange resin is taken from the group consisting of divinyl benzene cross-linked polystyrene-sulfonates and Na, $NH_4$ and K salts thereof. An N-saline solution is sprayed into the nasal cavity after administration of the powder to effect ion exchange of Na in the N-saline with the peptide from the resin for efficient delivery of the peptide.

4 Claims, 1 Drawing Sheet

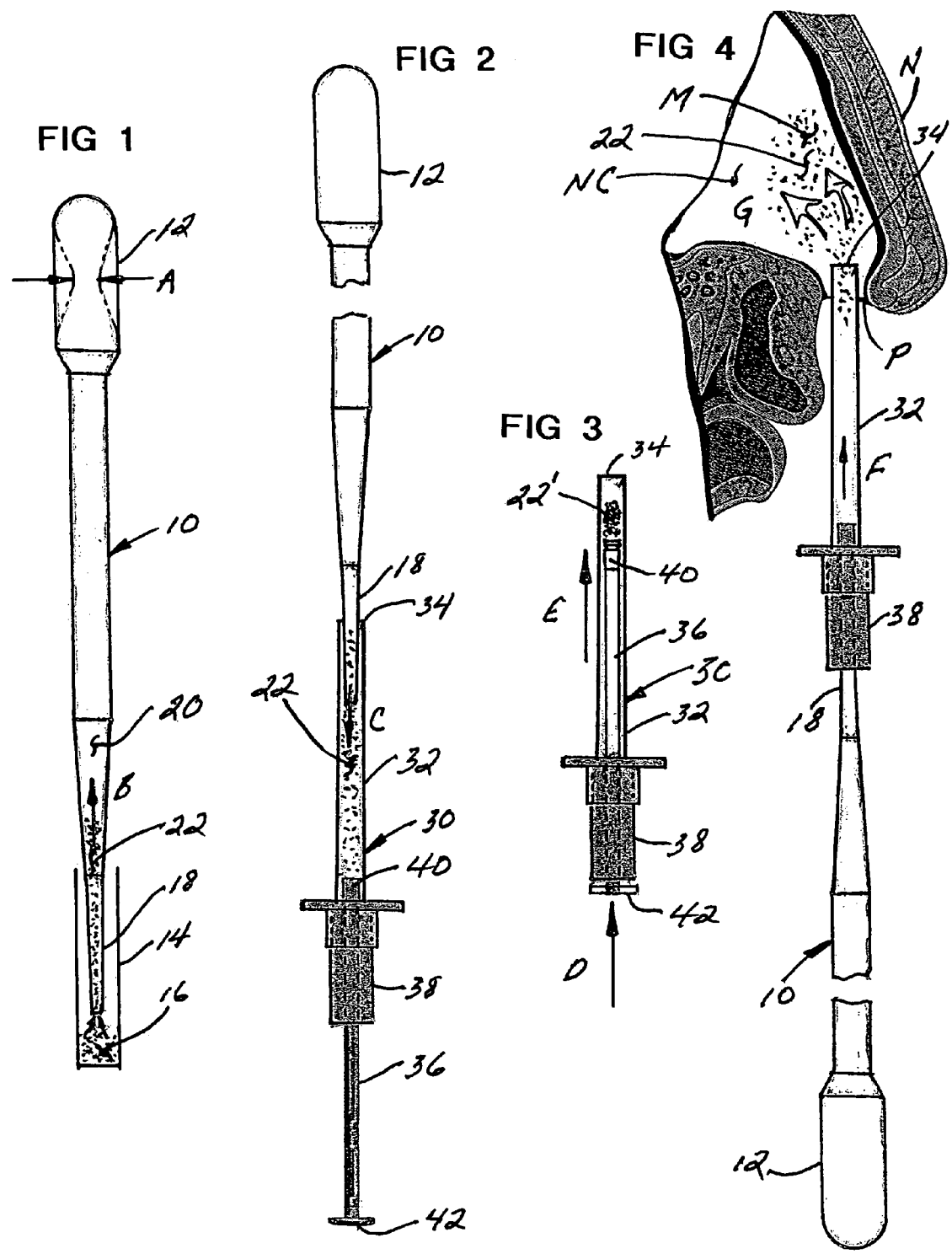

MEDICAMENT COMPOSITION AND METHOD OF ADMINISTRATION

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to medicament compositions for nasal administration of pharmacologically active peptides including Natrecor and Insulin, and more particularly to a unique such composition in a slightly moist form and for a system and method for administration of the composition.

2. Description of Related Art

Peptides such amino acid medications, Insulin, antibodies, recumbent DNA such as NATRECOR, stem cell preparations cannot be taken orally because the high acidic pH of the stomach destroys the medication activity. Therefore, such medications are traditionally administered by injection in combination with a transport media such as N-saline or N-glucose, insoluble solid suspensions as in the Reteculoendothyal (RE) system and an emulsion including insulin. Colloidal medical applications using the lung capillary as a bloodstream introduction mechanism are also becoming more widely accepted for introducing such peptides into the bloodstream.

A new form of insulin delivery without the need for injections has been developed by Generex Biotechnology Corporation in Toronto, Canada and is being marketed under the trade name ORALGEN. Oralgen is an Insulin formulation made for oral spray into the mouth by a special spray applicator carrying a trademark Rapid Mist Device. The insulin mist is thereby absorbed into the bloodstream through the mucous membranes in the mouth.

Prior U.S. patents provide an additional source for unique and distinctive compounds and techniques for administration of various newly developed drugs and pharmacologically active peptides.

U.S. Pat. No. 5,942,242 to Mizushima, et al. teaches a medicament for nasal administration for delivery of a vaccine or pharmacologically active peptide comprising a powder of one or more cation exchange resins to which a vaccine or pharmacologically active peptide is compounded. A novel insulin preparation, and more particularly an insulin preparation which is clinically suitable for nasal administration, is taught by Hirai, et al. in U.S. Pat. No. 4,153,689. Further limitations of this teaching relate to a failure to teach a true homogenous mixture which depends upon the mechanical binding of elements by VanDerVal-type binding which does not depend upon an ion exchange to effect transfer of the medicament into the nasal cavity.

A powdery pharmaceutical composition for nasal administration comprising a physiologically active polypeptide or its derivative and a water-absorbing, water-insoluble base is disclosed by Suzuki, et. al. in U.S. Pat. No. 4,613,500. U.S. Pat. No. 5,179,079 to Hansen, et. al. teaches a preparation for intranasal administration containing a pharmaceutically active polypeptide and an absorption enhancing system containing a fatty oil.

Illum is the inventor of seven (7) different U.S. patents directed to drug delivery compositions and formulations for nasal administration. U.S. Pat. No. 5,204,108 discloses a drug delivery composition comprising microspheres and an active drug while U.S. Pat. No. 5,629,011 teaches a composition for nasal administration of the polar metabolites of opioid analgesics. U.S. Pat. No. 5,648,095 teaches the preparation of microparticles and U.S. Pat. Nos. 5,707,644 and 5,804,212 are directed to small particle compositions for intranasal drug delivery. U.S. Pat. No. 5,690,954 discloses a drug delivery system containing microspheres, an active drug and a bioavailability improving material and U.S. Pat. No. 5,744,166 teaches drug delivery compositions.

Meezan, et al. in U.S. Pat. No. 5,661,130 teaches a method of increasing the absorption of a compound via the ocular, nasal, nasolacrimal or inhalation route into the circulatory system. A method of raising or lowering the blood glucose level by administering glucagon or insulin with absorption enhancers is further taught in '130.

Yanagawa discloses nasally administrable compositions in U.S. Pat. Nos. 5,603,943, 5,908,824, 6,197,328 and 6,589,559. The '943 patent teaches a nasally administrable composition with a physiologically active substance dispersed homogeneously in and onto a physiologically acceptable powdery or crystalline polyvalence metal compound carrier. The '824 patent teaches a composition containing a physiologically active peptide such as peptide hormone, physiologically active protein, enzymatic protein with a unique carrier that is highly absorbable into the body nasally. The nasally administrable composition of the '328 patent contains physiologically active compounds such as insulin, calcitonin, prostaglandin derivatives, monoclonal antibodies or interleukin derivatives. The '559 composition teaches a physiologically active substance dispersed homogeneously onto a fin powdery form of a cereal such as rice, wheat, soybean, corn, etc.

U.S. Pat. No. 5,997,848 to Patton, et al. teaches the delivery of insulin by inhalation of a dry powder form of insulin. A system and method for producing microparticles loaded with biologically active drugs for controlled release of the drugs in a nasal passageway is taught by Bomberger, et al. in U.S. Pat. No. 6,375,985.

A powdery nasal composition comprising a drug and colloidal cellulose is taught by Dohi, et al. in U.S. Pat. No. 6,428,805 and Vickery, et al., in U.S. Pat. No. 6,521,597 teaches intranasal administration of LHRH polypeptides in powdered form.

U.S. patent application Publication US 2002/0012688 A1 to Dohi, et al. discloses a powdery composition for nasal administration containing a drug, a water-absorbing base material such as hydroxypropyl cellulose and a water-absorbing and water-insoluble base material such as crystalline cellulose.

U.S. patent application Publication US 2004/0063615 A1 to Oki, et al. teaches an insulin-containing composition for nasal administration comprising a crystalline cellulose aggregate as a carrier.

European Patent EP0200383 invented by Campanale and Su, discloses a method for treatment of diabetes mellitus comprising a pharmaceutically acceptable amount of an alkali metal salt, or the free acid of a substantially zinc-free insulin in the presence of an absorption enhancing agent.

A formulation for nasal insulin delivery is further shown in the abstract of WO9422461 to Franciscus Merkus, as published in BE1006873 and AU6428994. Finally, WO 03/004048 A1 to Oki, et al. teaches granular compositions for nasal administration of insulin which comprise as a carrier aggregated crystalline cellulose.

Other compositions adapted for nasal administration are as follows:
U.S. Pat. No. 5,578,567 to Cardinaux, et al.
U.S. Pat. No. 5,725,852 to Igari, et al.
U.S. Pat. No. 5,948,749 to Igarashi, et al.
U.S. Pat. No. 6,416,742 to Stefely, et al.
U.S. Pat. No. 6,506,730 to Lee, et al.
U.S. Pat. No. 6,428,780 to Leone-Bay, et al.
U.S. Pat. No. 6,699,467 to Leone-Bay, et al.
U.S. Pat. No. 4,294,828 to Thominet, et al.

BRIEF SUMMARY OF THE INVENTION

This invention is directed to a medicament powder, system and method for nasal administration of a pharmacologically active peptide across the nasal mucous membrane. A free-flowing powder having a low moisture content includes a cross-linked cation exchange resin in anionic form and a pharmacologically active peptide in cationic form ionically bound together. The particles of the powder function as carriers of the peptide during nasal administration. The cation exchange resin is taken from the group consisting of divinyl benzene cross-linked polystyrene-sulfonates and Na, $NH_4$ and K salts thereof. An N-saline solution is sprayed into the nasal cavity after administration of the powder to effect ion exchange of Na in the N-saline with the peptide from the resin for efficient delivery of the peptide.

It is therefore an object of this invention to provide a unique medicament powder for the nasal administration of pharmacologically active peptides across the mucous membrane of the nasal cavity.

Still another object of this invention is to provide a system for the delivery of medicament powder into the nasal cavity with amplified effectiveness of delivery of the medicament into the bloodstream by the follow-up administration of an N-saline solution into the nasal cavity after the medicament powder has been dispersed.

Yet another object of this invention is to provide a method for transmucous nasal membrane administration of a pharmacologically active peptide, which method includes the administration of an N-saline spray solution after the medicament powder has been dispersed into the nasal cavity.

Still another object of this invention is to provide a medicament powder for nasal administration which enables the simultaneous ionic binding of multiple peptide medicaments onto the same resin.

In accordance with these and other objects which will become apparent hereinafter, the instant invention will now be described with reference to the accompanying drawings.

BRIEF DESCRIPTION OF THE SEVERAL VIEWS OF THE DRAWING(S)

FIGS. 1 to 4 describe the method and apparatus for dispersing a pharmacologically active peptide in substantially dry powder form into the nasal cavity.

DETAILED DESCRIPTION OF THE INVENTION

General

Terminal amino acid medications such as insulin antibodies, recumbent DNA and stem cell preparation, cannot be taken orally because the Ph of the stomach (gastric acids) will destroy the medicating activity. A pH of near 7.0 of the amino acid molecules such as peptides, proteins and neucholic acid is in a non-ionized form (low solubility). They present a difficult problem in intravenous application. Converting these molecular species of peptides into a cation with pH 3.0–6.5 using HCL and then applying these cations to a cation exchange resin sulfonated styrene divinyl benzene (carboxylic polymer and phosphoric polymer) and ionically binding the converted medication to a cation (peptide-protein-nuclified) to the resin is the primary stage of making the powder of this invention. The cation powder medication/resin is then applied to the capillary membrane of the nasal cavity so that the medicament on the resin administered onto the mucous membrane can ionically exchange the cation medication with $N_a+$ in an N-saline spray to quickly introduce the peptide medicament into the bloodstream of the nasal capillary and into the body.

To further activate the medicine and resin, a nasal spray of saline for nose moisture is used as the source of $Na^+$ ion which releases the cation medication to the bloodstream. Thus in a controlled manner, the present invention also provides a time released peptide medicament.

Resin Preparation

The preferred resin is polystyrene divinyl benzene in sulfonated spherical cross linked form. This final product is washed free of sulfuric acid ($H_2SO_4$) and shipped as a slightly damp resin, $RSO_3H$ in the acid form.

This off-the-shelf acid form of resin (R $SO_3H$) is low enough in pH=0 that peptide and proteins are broken down (like in the stomach) to single amino acids, destroying any medication—peptide—protein coming in contact with the acid resin form. Therefore, it must be first converted into a mildly acid form having a pH of 3.0–6.5 as follows:

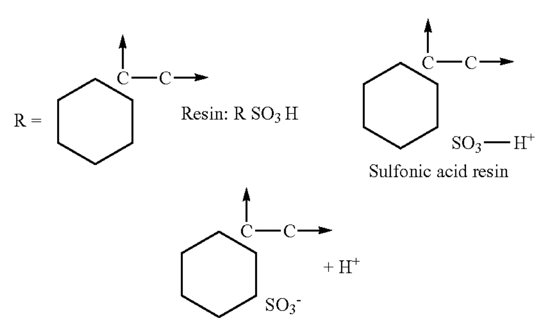

Anion Cation $R + H_2SO_4 \longrightarrow R\,SO_3H + H_2O$

Polymer + $H_2SO_4$ Polystyrene sulfonic acid resin

The chemical reaction for modifying the acid level of the commercially available resin is as follows:

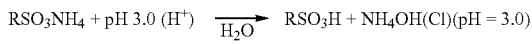

Details of Resin

The commercially available ion exchange resin selected is a polystyrene sulphonic 7.8% cross-linked divinyl benzene resin. The resin source is Dow Chemical; the resin is cross-linked between about 2% to 12% with a cross linking of 7.8% and a diameter of about 10–50 microns dia and exchanged with 0.5 m NaOH to 50% of the hydrogen ion capacity [$\phi SO_3Na$] and washed with deionized water. The washed resin is dried at 90° C. In place of NaOH, KOH, $NH_4OH$, $Mg(OH_2)$ can be used. The resin is dry to 5–10% moisture and ground in a Hammer Mill to 5 to 20 microns and stored.

Ammonium hydroxide was used to neutralize the hydrogen form of the resin to form an ammonium salt as follows.

$\phi$ represents the resin

The excess liquid was centrifuged off and the resin dried to 5% moisture as $R\ SO_3NH_4$.

An alternate example of polyvalent cation exchange resin is: $R\ SO_3)_2$ Magnesium Ion Exchange Resin acid-modified as follows:

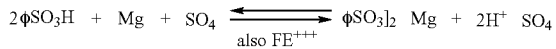

Hydrogen form [$\phi SO_3H$] of cross-linked polystyrene divinyl benzene sulfonic acid is equilibrated with excess magnesium sulfate (aqueous) [$Mg\ SO_4\ H_2O$] produced when the equilibrium reaction occurs. The reacted product $\phi SO_3)_2Mg.$ is DI water washed to free it of excess salt ($Mg\ SO_4$) After it is washed, the resin is dried for 24 hours at 95° C. into a clean substantially dry resin [$\phi SO_3)_2\ Mg$] preferably having only a small moisture content of up to 5%.

The charge on the polymer surface is controlled by the cross linking of the polymer and the ionic nature of it i.e. $\phi SO_3$ NATRECOR; $\phi SO_3\ NH_4\ \phi SO_3)_2\ Mg\ \phi SO_3)_3Fe$. The cross linking of the polymer resin is in the range of 2% to about 12%. The particle size dry is from 10–50 microns.

Peptides Tested

Two specific peptide/proteins are used in testing:
1. Insulin mol wt. 6000, Humulin N, Eli-Lilly France suspension 100 unit/ml injectable for diabetes
2. NATRECOR Mol wt. 3464 gm, U.S. Pat. Nos. 5,114, 923, 5,674,710 by Seios Sunnydale Calif. 1.5 mg Lyophilized soy solid containing 32 amino acid chain for treatment of high blood pressure.

For Insulin, test subjects were Type II diabetics requiring 10–20 units of well-mixed insulin suspension injected per day monitored by blood sugar level. For the NATRECOR test, intravenous injection subjects were of low heart capacity requiring 1.5 mg of NATRECOR to 100 ml of N-saline 3× per week.

Blood sugars were tested by taking a fresh drop of blood in a MEDISENSE test strip in a calibrated MEDISENSE precision Xta meter from Abbot Laboratories, Bedford, Mass. The readings are in mg/dl.

General Procedure—Preparation of Resin-Peptide

The cation formation of the resin-peptide/protein medication (e.g. Natrecor or Insulin) is as follows:
1. Separate dry (lyophilized) peptide/protein (the amount necessary for test).
2. Add aqueous HCl pH 3.0.
3. Place the cation formed peptide/protein into solution.
4. Take 0.4 mg prepared dried sample of the $R\ SO_3\ NH_4$ and add #3 in a dish and mix into a "mud like" mixture.
5. Vacuum dry sample into a free flowing powder.
6. Take this free flowing powder and deposit it in nose; then use an N-saline spray to activate ion exchange resin.

Ionic Binding and Release

The two chemical reactions for preparing the medicament/resin powder and its ion exchange reaction when applied to the nasal cavity are as follows:

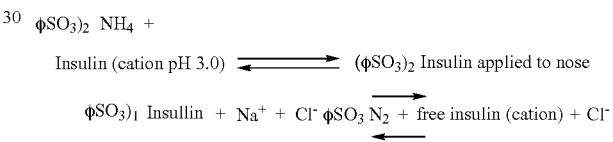

The free insulin cation goes into the blood stream via nose capillaries directly as ion form instead of the colloidal form (e.g. insulin at pH7).

Resin-Insulin Test Samples

A sample of 0.5 mg of the prepared resin is used for a final product of 0.1 mg/application for each on application of 0.1 mg of insulin and NATRECOR (0.5 mg of resin equaling 5 applications of each. Deionized water was microwaved for one minute to remove bacteria.

The test subject is a diabetic required a 24 hour injection cycle of a minimum of 15 units of humulin N insulin preceding a mealtime [Eli Lilly & Co]. The 0 test sample is the start time of either an injection or a nasal application. Injection as compared to nasal application techniques.

EXPERIMENT I

Insulin by Nasal Administration

| TIME | ACTIVITY | BLOOD GLUCOSE (ms/g) |
|---|---|---|
| 7:05 pm | Dinner | |
| 9:20 pm | Blood Sugar | 138 |
| 11:00 pm | 2 Squirts of N Saline | |
| 1:00 am | Blood Sugar | 175 |

-continued

| TIME | ACTIVITY | BLOOD GLUCOSE (ms/g) |
|---|---|---|
| 6:50 am | Egg Bacon; then apply N Saline | |
| 8:15 am | Blood Sugar | 155 |
| 8:15 am | N Saline | |
| 9:10 am | Blood Sugar | 178 |
| 9:15 am | Breakfast | |
| 10:25 am | Blood Sugar | 283 |
| 10:40 am | Nasal app. of Insulin | |
| 11:10 am | Blood Sugar | 228 |
| 11:35 am | Blood Sugar | 222 |
| 11:35 am | N Saline Ion Exchange | |
| 12:00 pm | Blood Sugar | 188 |
| 1:30 pm | Lunch | 229 |
| 2:30 pm | Blood Sugar | 165 |
| 3:30 pm | Blood Sugar | 168 |
| 3:30 pm | N Saline | |
| 4:40 pm | Blood Sugar | 144 |
| 6:30 pm | Blood Sugar | 173 |
| 6:30 pm | N Saline | |
| 7:00 pm | Dinner | |
| 10:30 pm | Blood Sugar | 227 |
| 10:45 pm | 20 units Insulin injected | |
| DAY 2 | | |
| 2:30 am | Blood Sugar | 155 |
| 1:10 pm | To Blood Sugar 169/mg/dl No injected insulin for 12 hours | 169 |
| 1:25 pm | Nasal application of insulin-resin | |
| 1:55 pm | Blood Sugar | 157 m/dc |
| 2:30 pm | Blood Sugar Apply N-saline - 2 squirts in each nostril | 195 m/dc |
| 3:00 pm | Blood Sugar | 162 |
| 5:00 pm | Blood Sugar | 132 |
| 7:00 pm | Blood Sugar | 121 |

EXPERIMENT II

Insulin Application—Human Subject

In this experiment, a direct comparison is made between injection of insulin and nasal insulin administration in powder form. A sample of 0.5 grams of dry (5–10% moisture) 7.8% cross linked cation exchange resin (polystyrene divinyl benzene sulfonated resin in a $Na^+$—$NH_4^+$$Mg^{++}$ ion form, 5 to 30 microns. Mix in 75 units of Insulin I diluted (0.75 ml insulin+75 ml deionized water pH 3.0) w/HCl. The 1.25 total liquid is mixed with the dry resin (0.5 grams+1.25 grams total weight). After uniform mixing, the damp material is vacuum dried at 30" Hg, room temp. to remove about 95% of moisture. An overnight vacuum drying will accomplish this dry state. The dry insulin loaded resin is repowdered by a mild grinding in a mortar and pestle. The ground dry loaded resin loaded with insulin or Natrecor is sealed and stored.

| Time | Blood glucose ms/g |
|---|---|
| Insulin by Injection 15 units of insulin subcutaneously applied by injection. | |
| 0 insulin application | 180 |
| 15 minutes | 150 |
| 30 minutes | 144 |
| 1 hour | 150 |
| 1 hour 30 minutes | 154 |
| 7 hours | 135 |

-continued

| Time | Blood glucose ms/g |
|---|---|
| Insulin by Nasal Administration 15 units insulin on 0.100 g resin nasally applied | |
| 0 nasal application | 185 |
| 15 minutes | 156 |
| 1 hour | 150 |
| 2 hours | 140 |
| 3 hours | 140 |
| 4 hours | 135 |
| 5 hours | 134 |
| 12 hours | 154 |
| Repeat - Insulin by Nasal Administration | |
| 0 | 183 |
| 2 hours | 137 |
| 3 hours | 144 |
| 5 hours | 149 |

Resin-NATRECOR Test Samples

The test human had been on injected non-ionic NATRECOR for 5 weeks at two applications per week. The NATRECOR had been dissolved in N (normal) Saline (pH of 7) [1.5 mg—3 applications at 65 cc/application of N-saline]. The heart function had been correlated during this application.

The human test had thereafter been off of injected NATRECOR for 4 weeks. A sample of 0.1 grams of resin NATRECOR will be nasally applied. To determine if the NATRECOR moves across the nasal membrane and into the bloodstream, blood pressure was monitored, a decrease in blood pressure indicating that the NATRECOR has come from the resin peptide powder into the nasal cavity and has entered the bloodstream.

A sample of 1.5 mg of hydrophilized NATRECOR was dissolved in 1.5 mg of deionized water. This solution was loaded on 0.5 grams dry (5 to 30 microns) ion exchange cation resin 2% to 12% X-L and uniformly mixed damp. The damp sample is vacuum dried at room temperature at 30" Hg overnight.

Loading of Resin wt. 1.400 g. $H_2O$+0.5 gm resin=2.15 g. wet or 0.515 g dry loaded resin. The dried resin+NATRECOR was reduced to powder by mortar and pestle and sealed and stored at 5° C.

Sample Prep

Five (5) samples of Natrecor at 1.5 mg. were diluted with 3.0–4.0 pH (HCl) to make 20 resin loaded test samples.

EXPERIMENT III

NATRECOR by Nasal Administration

| TIME | BLOOD PRESSURE | ACTIVITY |
|---|---|---|
| TEST 1 | | |
| START | 155/57 | Nasal application |
| at 20 min. | 149/57 | Na Cl added spray |
| at 35 min. | 146/59 | Na Cl spray |
| at 60 min. | 150/64 | |

-continued

| TIME | BLOOD PRESSURE | ACTIVITY |
|---|---|---|
| TEST 2 | | |
| START | 168/61 | Nasal application |
| at 10 min. | | Na Cl spray |
| at 15 min. | 185/62 | |
| at 40 min. | 157/67 | |
| TEST 3 | | |
| START | 159/61 | |
| at 2 min. | 159/61 | Nasal application |
| at 17 min. | 153/60 | Na Cl spray |
| at 32 min. | 143/56 | Na Cl spray |
| at 58 min. | 160/68 | |
| TEST 4 | | |
| START | 179/66 | Nasal application |
| at 30 min. | 148/68 | Na Cl spray |
| TEST 5 | | |
| START | 167/68 | Nasal application + Na Cl spray |
| | $\phi\ SO_3\ NH_4 + Na\ Cl$ | |
| at 5 min. | 159/66 | |
| at 13 min. | 146/60 | |

METHOD AND APPARATUS FOR ADMINISTRATION

Referring now to the drawings, the preferred method and apparatus for dispensing of the medicament powder containing the peptide ionically bound to the resin is there shown. In FIG. 1, a flexible plastic syringe which is coated on the inner surface with carbon to prevent stickiness is utilized to initially draw a quantity 22 of the medicament powder 16 from an open vial 14. When the large flexible bulb 12 is finger squeezed in the direction of arrow A and then released with the tip 18 is in contact with the medicament powder 16, the quantity 22 of the loose powder is drawn upwardly in the direction of arrow B into the interior 20 of the flexible syringe 10.

In FIG. 2, the medicament powder 22 is then deposited into a slender syringe 30 which has been modified to have an enlarged open end 34 of the barrel 32 with the syringe needle removed. The tip 18 is inserted into the open end 34 as shown and then the bulb 12 is again finger squeezed to dispense the loose medicament powder 22 into the barrel 32 of the syringe 30. This step is accomplished with the syringe plunger 36 fully withdrawn but not removed by pulling on the enlarged head 42 into the position shown.

In FIG. 3, the head 42 of the plunger 36 is moved slowly upwardly in the direction of the arrow D so that the sealed tip 40 of the plunger 36 moves the medicament powder 22 in the direction of arrow D into a lightly packed plug or clump 22'.

In FIG. 4, the plunger 36 has been removed from the syringe 30 and the clump or plug 22' of lightly compacted medicament powder 22' remains in the position shown from FIG. 3. Thereafter, the tip 18 of the flexible syringe 10 is inserted into a flexible sleeve 38 for sealing engagement therewithin and in fluid contact with the interior of the barrel 32.

Still referring to FIG. 4, the open end 34 of the tubular body 32 is then inserted into a nostril P of the patient's nose N. When approximately in the position shown in FIG. 4, the flexible bulb 12 is again squeezed to propel air in the direction of the arrow F and to force the discharge and dispersion of the medicament powder 22 in the direction of arrows G to become attached to the mucous membrane M of the nasal cavity NC.

After the medicament powder 22 has been dispersed onto the mucous membrane M, a final step of spraying a quantity of N-saline into the nasal cavity in a fashion similar to that of FIG. 4 is then accomplished so as to further activate the ionic release of the peptide medicament from the powder 22 through the mucous membrane M as previously described.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

The invention claimed is:

1. A medicament powder for nasal administration to deliver a pharmacologically active peptide across the mucous membrane, comprising:
    a substantially free-flowing powder including an anionic form of a cross-linked cation exchange resin and a cationic form of a pharmacologically active peptide, said resin and said peptide being ionically bound together; the particles of said powder functioning as carriers of said peptide during nasal administration of said medicament;
    wherein said cation exchange resin is selected from the group consisting of divinyl benzene cross-linked polystyrene-sulfonates and $Na^+$, $NH_4^+$ and $K^+$ salts thereof;
    wherein said pharmacologically active peptide is nesiritide.

2. A medicament system for nasal administration to deliver a pharmacologically active peptide across the mucous membrane, comprising:
    a substantially free-flowing powder including a cross-linked cation exchange resin in anionic form and a pharmacologically active peptide in cationic form, said resin and said peptide being ionically bound together the particles of said powder functioning as carriers of said peptide during nasal administration of said medicament; wherein said cation exchange resin is taken from the group consisting of divinyl benzene cross-linked polystyrene-sulfonates and $Na^+$, $NH_4^+$ and $K^+$ salts thereof; an N-saline solution for sprayed administration into the nasal cavity to effect ion exchange of $Na^+$ in said N-saline with the peptide from said resin wherein said pharmacologically active peptide is nesiritide.

3. A medicament powder for nasal administration to deliver a pharmacologically active peptide across the mucous membrane formed by the process of: forming a first aqueous solution of an anionic form of a cross-linked cation exchange resin having a pH adjusted to between 3.0–6.5; forming a second aqueous solution of a cationic form of a pharmacologically active peptide having a pH adjusted to between 3.0–6.5; mixing said first and second aqueous solutions together, mixing said first and second aqueous solutions to form a free-flowing powder wherein said resin and said peptide are ionically bound together; wherein the particles of said powder functioning as carriers of said peptide during nasal administration of said medicament; wherein said pharmacologically active peptide is nesiritide.

4. A medicament powder as set forth in claim 3, wherein:
    said cation exchange resin being selected from the group consisting of divinyl benzene cross-linked polystyrene-sulfonates and $Na^+$, $NH_4^+$ and $K^+$ salts thereof.

* * * * *